United States Patent [19]

Hurst et al.

[11] 4,376,824
[45] Mar. 15, 1983

[54] PROCESS FOR PRODUCING GLUCOSE/FRUCTOSE SYRUPS FROM UNREFINED STARCH HYDROLYSATES

[75] Inventors: Louis S. Hurst; Norman E. Lloyd, both of Clinton, Iowa

[73] Assignee: Nabisco Brands, Inc., New York, N.Y.

[21] Appl. No.: 258,183

[22] Filed: Apr. 27, 1981

[51] Int. Cl.³ .............................................. C12P 19/24
[52] U.S. Cl. ...................................................... 435/94
[58] Field of Search ............................ 435/94, 96, 99

[56] References Cited

U.S. PATENT DOCUMENTS

| | | | |
|---|---|---|---|
| 3,551,293 | 12/1970 | Seidman et al. | 435/99 |
| 3,654,081 | 4/1972 | Vance et al. | 435/99 |
| 3,663,369 | 5/1972 | Morehouse et al. | 435/99 |
| 3,783,100 | 1/1974 | Larson et al. | 435/95 |
| 3,853,706 | 12/1974 | Armbruster | 435/99 |
| 3,909,354 | 9/1975 | Thompson et al. | 435/94 |
| 3,912,590 | 10/1975 | Slott et al. | 435/99 |
| 4,025,389 | 5/1977 | Poulsen et al. | 435/94 |
| 4,230,802 | 10/1980 | Ehrenthal et al. | 435/94 |
| 4,235,965 | 11/1980 | Walon | 435/95 |
| 4,284,722 | 8/1981 | Tamuri et al. | 435/94 |

OTHER PUBLICATIONS

Hollo et al., Starke 27, No. 7, 232–235, (1975).
Linko et al., Enzyme Microb. Technol., vol. 1, 1979, pp. 273–278.
G. B. Madsen et al., "A New, Heat Stable Bacterial Amylase and its Use in High Temperature Liquefaction", *Die Starke*, vol. 25, No. 9, 1973, pp. 304–308.
B. L. Scallet et al., "Studies in the Isomerization of D–Glucose", *Die Starke*, vol. 26, No. 12, 1974, pp. 405–408.
B. J. Schnyder, "Continuous Isomerization of Glucose to Fructose on a Commercial Basis", *Die Starke*, vol. 26, No. 12, 1974, pp. 409–412.
N. H. Aschengreen, "Production of Glucose/Fructose Syrup", *Process Biochemistry*, May 1975, pp. 17–19.
C. Bucke, "Industrial Glucose Isomerase", In *Topics in Enzyme Fermentation and Biotechnology*, A. Wiseman, Ed., vol. 1, Chap. 7, 1976.
N. H. Aschengreen et al., "Liquefaction, Saccharification, and Isomerization of Starches from Sources Other than Maize", *Starch*, vol. 31, No. 2, 1979, pp. 64–66.

*Primary Examiner*—Lionel M. Shapiro
*Attorney, Agent, or Firm*—Richard Kornutik; Henry S. Wyzan; Robert A. Conzett

[57] ABSTRACT

A glucose/fructose syrup is produced by enzymatically isomerizing an unrefined starch hydrolysate. The hydrolysate is prepared under controlled liquefaction and saccharification conditions to provide an isomerization substrate wherein the concentrations of calcium ions and non-enzymatically generated ketose sugars are maintained at low levels.

33 Claims, No Drawings

PROCESS FOR PRODUCING GLUCOSE/FRUCTOSE SYRUPS FROM UNREFINED STARCH HYDROLYSATES

BACKGROUND OF THE INVENTION

This invention relates to a process for producing glucose/fructose syrups. More particularly, this invention relates to a process for producing glucose/fructose syrups comprising treating an unrefined glucose-containing starch hydrolysate with immobilized glucose isomerase.

Methods for producing glucose-containing starch hydrolysates are well known in the art and broadly fall into two categories: the acid-enzyme and enzyme-enzyme conversion processes. The latter process is generally preferred since it results in less reversion products being formed which are resistant to further treatment and therefore reduce the overall efficiency of the process.

In the enzyme-enzyme process an aqueous slurry is formed containing from about 30 to 40 percent dry substance starch and a starch digesting enzyme, typically bacterial alpha-amylase, is added thereto and the slurry heated to a temperature in the range of 80° to 90° C. to partially hydrolyze or liquefy the starch. Alpha-amylase is an endo-amylolytic enzyme capable of promoting random cleavage of $\alpha$-1,4-glucosidic bonds within the starch molecule and is elaborated by a number of types of microorganisms, e.g., members of the Bacillus and Aspergillus genera, and also is present in malted cereal grains.

Alpha-amylase treatment results in only partial hydrolysis of the starch molecule since this enzyme does not act upon the $\alpha$-1,6-glucosidic bonds in the molecule to a significant degree. Thus, alpha-amylase treated starch largely comprises oligosaccharides of varying molecular weights and fragments thereof which are more susceptible to further digestion by product-specific enzymes than is the untreated starch. To further hydrolyze the starch to provide a hydrolysate containing a significant proportion of glucose, the liquefied starch is treated with a glucogenic enzyme. Conventionally, the glucogenic enzyme employed is glucoamylase.

In the acid-enzyme process starch is first partially hydrolyzed or liquefied, e.g., by forming an aqueous suspension containing about 35 to 40 percent starch and incorporating therein an acid such as hydrochloric acid. The acidified suspension is then heated to high temperatures, cooled and treated with glucoamylase at a suitable concentration and pH to convert the partially hydrolyzed starch to glucose.

The use of glucose isomerase adsorbed onto or bonded to carriers to provide immobilized biological catalysts has largely superseded older methods whereby soluble enzymes or whole cells of microorganisms were utilized. In general, immobilized enzymes provide a number of advantages over these older methods, particularly in commercial systems for carrying out continuous conversion processes. Because of the economics involved in the utilization of such systems, it is of utmost importance that the stability or effective life of the immobilized enzyme be maintained over a period sufficient to permit conversion of large quantities of substrate. Methods of preparing immobilized glucose isomerase include bonding or otherwise adhering the enzyme to inert carriers such as derivatized cellulose, ion exchange resins and other polymeric materials, encapsulating the enzyme, entrapping the enzyme within fibers, etc.

Hitherto, attempts to use unrefined starch hydrolysates as substrates in continuous enzymatic processes for producing glucose/fructose syrups have not been efficient as desired due to the fact that the immobilized glucose isomerase becomes inactivated to a substantial degree after a relatively short period of use. This is believed to be due largely to the presence in the unrefined starch hydrolysate of materials which inhibit or otherwise deleteriously affect the activity of this enzyme.

Our investigation indicates that the stability or effective life of immobilized glucose isomerase is reduced by the presence in the unrefined starch hydrolysate of materials formed during the processes conventionally employed to liquefy and saccharify the starch. Although these materials have not been completely characterized, we believe that conditions for preparing starch hydrolysates which enhance the formation of such materials also tend to promote the non-enzymatic formation of ketose sugars, such as maltulose and fructose, or their precursors. The total concentration of either or both of these sugars, when produced by non-enzymatic action in an unrefined hydrolysate, therefore, can serve as an index of the suitability of the hydrolysate for enzymatic isomerization insofar as the prolongation of the activity of glucose isomerase is concerned.

It has hitherto been the general practice in the art to extensively refine or purify glucose-containing starch hydrolysates by known methods prior to isomerization of the glucose with glucose isomerase. Refining procedures commonly utilized include treatment of the clarified hydrolysate with carbon and ion exchange materials to remove undesirable constituents including metallic ions and carbohydrate degradation products.

Starch liquefaction processes are generally carried out at high temperatures in order to insure complete gelatinization of the starch granules. Liquefactions utilizing calcium dependent alpha-amylase preparations, e.g., those derived from *B. subtilis,* may require the presence of as much as 200 ppm of calcium ions, based on dry substance starch (dss), to impart optimum heat stability to this enzyme. Calcium in the form of lime has frequently been used for this purpose in starch liquefactions wherein it also serves to adjust the pH to the desired levels. However, the presence of substantial levels of calcium ions results in an undesirably high ash content in the hydrolysate and also, the calcium ion is a known inhibitor of glucose isomerase activity. Although it is probably impossible to avoid the presence of calcium altogether in starch hydrolysates prepared with alpha-amylase, for the purposes of the present invention, the hydrolysate should contain a concentration of not more than about 100 ppm of calcium ions, based on the content of the starch.

By carefully controlling the conditions under which the hydrolysate is prepared and avoiding those which promote the development therein of non-enzymatically generated ketose sugars as well as a high ash content, expensive procedures for refining or purifying the hydrolysate prior to isomerization with immobilized glucose isomerase may be eliminated with no significant reduction in the stability or effective life of the enzyme.

THE PRIOR ART

The state of the art relating to the enzymatic liquefaction and saccharification of starch to provide glucose-containing hydrolysates suitable for enzymatic conversion to glucose/fructose syrups is succinctly set forth in an article by N. H. Aschengreen, et al. in *Starke*, Vol. 31, pp. 64–66 (1979). This article discloses a four stage process for converting a starch into a fructose syrup: (1) Liquefaction; (2) Saccharification; (3) Purification; and (4) Isomerization. The first step in preparing the hydrolysates, liquefaction or thinning of the starch, comprises treating a starch slurry with alpha-amylase at a temperature of about 105° C. for a period of about 5 minutes and at a pH of 6 or above. It is also disclosed that a substantial level of calcium ions is desirable in the slurry during liquefaction to maintain the activity of the alpha-amylase at the high temperatures employed. It is also specifically recommended that a minimum of 40 ppm $Ca^{++}$ be present in a 30–35 percent dss slurry during liquefaction. This is equivalent to 114–135 ppm based on the dry weight of starch. Following further heat treatment, the partially hydrolyzed starch is treated with a glucogenic enzyme to provide a hydrolysate having a high glucose content. The glucose-enriched hydrolysate is clarified, refined and treated with glucose isomerase to convert a portion of the glucose to fructose.

As stated in the aforementioned article, it has been the general practice in the art to subject glucose conversion syrups prepared from starch hydrolysates to extensive refining procedures prior to isomerization with glucose isomerase in order to remove materials which adversely affect the stability of the enzyme as well as materials which contribute undesirable color in the finished syrup. Typically, as noted in the article, starch hydrolysates are treated with both carbon and ion exchange materials prior to isomerization with glucose isomerase.

Other pertinent art includes an article by C. Bucke in *Topics in Enzyme Fermentation and Biotechnology*, A. Wiseman, editor, Vol. 1, Chap. 7 (1976) wherein the quality of the glucose feedstuffs as substrate for glucose isomerase conversions is discussed. In *Die Starke*, Vol. 25, No. 9, pp. 304–308 (1973) Madsen, et al. describe a heat stable alpha-amylase preparation having reduced calcium dependence for stability at high temperatures. U.S. Pat. No. 4,025,389 to Poulsen, et al. teaches a process for enzymatically isomerizing glucose-containing syrups to glucose/fructose mixtures wherein a starch hydrolysate having limited concentrations and proportions of calcium and magnesium ions is utilized. U.S. Pat. No. 4,230,802 to Ehrenthal, et al. relates to a method for utilizing an unrefined glucose syrup as substrate for the enzymatic isomerization of glucose to fructose. The substrate containing starch conversion mud is isomerized without the addition of cobalt and/or magnesium salts. U.S. Pat. No. 4,235,965 to Walon is directed to a process for preparing liquefied starch at high solids concentrations utilizing alpha-amylase derived from *Bacillus licheniformis*. A review of the production of glucose/fructose syrups on a commercial basis is given by B. J. Schnyder in *Die Starke*, Vol. 26, No. 12, pp. 409–412 (1974). Exemplary of the many patented processes for enzymatically isomerizing glucose-containing starch hydrolysates with immobilized glucose isomerase is U.S. Pat. No. 3,909,354 to Thompson, et al. Processes for preparing low DE starch hydrolysates by two stage liquefaction techniques are taught, for example, in U.S. Pat. Nos. 3,551,293; 3,654,081; 3,663,369, 3,783,100; 3,853,706 and 3,912,590 and German Pat. No. 2,216,854.

Purifying or refining of starch hydrolysates prior to isomerization is disclosed in the above noted articles by Aschengreen, et al. and by Schnyder as well as in articles by Scallet, et al., *Die Starke*, Vol. 26, No. 12, pp. 405–408 (1974) and by Aschengreen, *Process Biochemistry*, May 1975, pp. 17–19.

OBJECTS OF THE INVENTION

It is a principal object of the present invention to provide a process for enzymatically isomerizing glucose in an unrefined glucose-containing starch hydrolysate to fructose.

It is another object of the present invention to provide a process for enzymatically isomerizing glucose in an unrefined glucose-containing starch hydrolysate to fructose wherein the hydrolysate is prepared under conditions which provide therein low levels of materials which adversely affect the stability of glucose isomerase.

It is yet another object of the present invention to provide a process for enzymatically isomerizing glucose in an unrefined glucose-containing starch hydrolysate to fructose wherein the hydrolysate contains low levels of calcium ions and of non-enzymatically generated ketose sugars.

Other objects and advantages of the present invention will be apparent from a reading of the specification and the appended claims.

SUMMARY OF THE INVENTION

Starch is liquefied and enzymatically saccharified under carefully controlled conditions to provide a glucose-containing hydrolysate having present not more than about 100 ppm of calcium ions, based on dry substance starch, and wherein the mole ratio of non-enzymatically generated ketose sugars is less than about 2 (moles per 100 moles of hexose units). A glucose/fructose syrup is prepared by contacting the unrefined hydrolysate with immobilized glucose isomerase.

DETAILED DESCRIPTION OF THE INVENTION

Attaining the objects of the present invention requires careful control of the conditions under which the starch hydrolysate is prepared.

Starch obtained from conventional sources, e.g., the wet milling of corn, is washed and an aqueous slurry thereof prepared containing 30 to 35 percent dry substance starch. Preferably, the slurry will have a low ionic content, e.g., not more than about 0.2 percent as sulfated ash, dry basis. Other starches obtained from both root and cereal sources may also be used for preparing the hydrolysate including potato, tapioca, wheat, sorghum and waxy maize starches.

The glucose-containing starch hydrolysates of the present invention may be produced by an acid-enzyme process or an enzyme-enzyme process. In the acid-enzyme process, the starch is first liquefied by a mild acid treatment, and then an enzyme is used to convert the liquefied starch to glucose. In the typical enzyme-enzyme process, the starch is liquefied by treatment with an alpha-amylase, and then a glucoamylase is utilized to convert the liquefied starch to glucose. It is preferred to use the enzyme-enzyme process to produce the glucose-containing starch hydrolysate.

The production of glucose-containing starch hydrolysates which do not need refining prior to being treated with immobilized glucose isomerase requires careful control of reaction conditions during liquefaction and saccharification. The temperature, time and pH employed should be such as to inhibit the formation of substantial amounts of materials which adversely affect the stability of glucose isomerase.

It is also necessary that the calcium content of the substrate for isomerization be minimized. It is well known that some alpha-amylase preparations require the presence of a high calcium ion concentration to achieve activity during liquefaction. When a high concentration of calcium is present during liquefaction, it is necessary to remove the calcium ions from the hydrolysate prior to isomerization. Any known method for removing ionic calcium may be used, such as treatment of the glucose-containing liquor with oxalic acid followed by filtration.

It is preferred to utilize an alpha-amylase preparation during liquefaction which does not require the presence of a high concentration of added calcium ions for activation and heat stability. Satisfactory results have been obtained utilizing an alpha-amylase preparation derived from *Bacillus licheniformis* (Termamyl-60L alpha-amylase; Novo Enzyme Corp.) This preparation is characterized by good thermal stability and activity over a wide pH range as well as having reduced dependence upon the presence of calcium. Other suitable alpha-amylase preparations which may be used are Taka-Therm (Miles Laboratory, Elkhart, Ind.) and Hi-Tempase (Biocon Inc., Lexington, Ky.).

The period during which gelatinization and liquefaction of the starch are carried out and the temperature employed are interdependent. If the starch slurry is heated at low gelatinization temperatures for too short a period, a substantial quantity of the more heat resistant starch granules may remain ungelatinized so that the alpha-amylase is not as effective as desired in reducing the viscosity of the slurry. In general, the use of temperatures in the lower part of the gelatinization range, e.g., below about 80° C. for corn starch, provides unsatisfactory results due to the substantial amount of starch that remains ungelatinized, and therefore is substantially inaccessible to enzyme action. Of course, since the gelatinization is effected in the presence of the alpha-amylase, the temperatures employed must not be so high as to adversely affect the activity of the enzyme preparation utilized.

Particularly important is the maintenance of reaction conditions during liquefaction and saccharification which do not promote the chemical or non-enzymatic production of ketose sugars. More specifically, conditions should be maintained which provide a hydrolysate having present a calcium ion concentration of not more than about 100 ppm based on dry substance starch and a mole ratio of non-enzymatically generated ketose sugars of less than about 2. It is preferred that the hydrolysate contain a calcium ion concentration of not more than about 30 ppm and a mole ratio of non-enzymatically generated ketose sugars of less than about 1. "Mole Ratio" is defined as the moles of non-enzyme generated ketose sugars per 100 moles of hexose units. Because the effects of temperature, time and pH during liquefaction are interdependently related, these factors must be controlled within relatively narrow ranges.

The polymeric structure of granular starch is not affected to an appreciable extent by alpha-amylase until the granules become gelatinized. Gelatinization is effected by heating the starch in water to a temperature range within which the granules swell and the forces binding the starch molecules together are weakened sufficiently to cause gelatinization. Generally, since alpha-amylases are heat sensitive and tend to become denatured at temperatures above 100° C., temperatures below 100° C. are utilized during liquefaction in order to prolong the efficacy of the enzyme. Because the forces that bind the starch molecules in the granule form vary in strength, some granules are gelatinized at temperatures below 100° C. and become susceptible to the action of the alpha-amylase while others remain ungelatinized and are still resistant to such enzyme action. As a result, it is preferred to liquefy the starch with alpha-amylase in two stages with a very brief intervening autoclaving step. During the first stage, the starch is partially gelatinized and liquefied to a limited extent to provide a partial hydrolysate. The purpose of the autoclaving step is to gelatinize any resistant starch granules which were not gelatinized during the first liquefaction stage. The starch hydrolysate is then further thinned to the desired level in the second liquefaction stage.

In the present process, it is important to maintain the substrate at a pH of about 6.0 or lower during liquefaction. At a pH level above about 6.0, degradation products that will inhibit isomerase activity may be formed, particularly where high temperatures and/or prolonged reaction periods are utilized. The liquefaction is advantageously carried out in two stages at a pH in the range of about 5.0 to 6.0 and preferably in the range of about 5.2 to about 5.4 and at temperatures which are within the gelatinization range of the starch, and are also suitable for the enzyme liquefaction of the starch. In the case of wet milled corn starch, it is usually necessary to adjust the pH upward to the desired range of liquefaction. Calcium compounds, e.g., lime or calcium carbonate, are commonly used to adjust the pH during liquefaction with alpha-amylase, especially in reactions wherein calcium dependent alpha-amylase preparations are utilized. Since calcium adversely affects the activity of glucose isomerase, it is preferred to avoid the overt addition of a source of calcium ions to the hydrolysate. However, if calcium ions are added, it will be necessary to remove them before isomerization, if the objects of the invention are to be realized. Although there are a number of materials which may be used to adjust pH during the liquefaction reaction, advantageously, soluble magnesium compounds are used for this purpose since glucose isomerase derived from a number of microorganisms requires magnesium for optimum activity.

The amount of alpha-amylase incorporated into the slurry will depend upon a number of factors but is principally determined by the inherent activity of the enzyme preparation, the concentration of starch in the slurry, and the extent of amylolytic conversion desired. Generally, in a two-stage liquefaction system similar or somewhat lesser amounts of alpha-amylase activity are incorporated into the second stage relative to the first stage. When an autoclaving treatment is intervened between the two stages, any residual alpha-amylase activity in the first stage is substantially destroyed. Typically, from about 6 to about 10 liquefons of alpha-amylase activity per gram of dry substance starch will be provided in the first stage, and from about 5 to about 10 liquefons of alpha-amylase activity, on the same basis, will be provided in the second stage.

The liquefaction temperatures utilized in both stages are preferably below about 100° C., more preferably in a range of about 82° to about 95° C., and most preferably in a range of about 84° to about 88° C. At liquefaction temperatures within the above ranges, satisfactory results have been achieved using heating periods of from about 1 to about 3 hours.

The first liquefaction stage provides a partial hydrolysate having a DE preferably in the range of about 6 to about 12. Following the first liquefaction stage, the slurry may be subjected to an autoclaving treatment to provide a partial hydrolysate which is substantially free of ungelatinized starch. Prolonged exposure of the partially liquefied starch to autoclaving conditions results in the formation of substances which are deleterious to glucose isomerase and need to be removed prior to isomerization to prolong its stability. Therefore, the autoclaving time and temperature should not exceed a period of about 2 minutes and a temperature of about 160° C., respectively. The preferred autoclaving conditions are a temperature of about 125° C. and a period of about 1 minute.

Since the alpha-amylase present in the first liquefaction stage is substantially inactivated by the autoclaving treatment, it is necessary to incorporate additional enzyme into the second liquefaction stage. Usually, the amount of the alpha-amylase incorporated will be similar to that utilized in the first stage. During the second stage, the starch granules, substantially all of which are now gelatinized, are readily acted upon by the enzyme under the set forth conditions to provide a thinned hydrolysate preferably having a DE of from about 14 to about 20 and which is substantially free of raw or retrograded starch. Typically, the hydrolysate will have a DE of about 16.

The liquefied starch preparation is then treated with a glucogenic enzyme under suitable conditions to enzymatically convert the partially hydrolyzed starch to glucose. Typically, the enzyme utilized for this purpose is glucoamylase (also referred to as amyloglucosidase, glucamylase, glucogenic enzyme, etc.). Glucoamylase, which is produced by a number of types of microorganisms, is an exo-amylolytic enzyme which catalyzes the sequential hydrolysis of glucose moieties from the non-reducing ends of starch or amylodextrin molecules. Among the glucoamylase producing microorganisms are certain strains of fungi belonging to the Aspergillus genus, strains of the Rhizopus genus, and strains of Endomyces genus.

Saccharification of the liquefied starch preparation is carried out under conditions which result in a high rate of conversion of the starch to glucose. Preferably, the hydrolysate will comprise greater than 92 percent glucose and most preferably will have a glucose content above about 94 percent. Also, conditions should be such as do not promote resynthesis of the liberated glucose molecules to form oligosaccharides as is known to occur in saccharification reactions using glucoamylase.

The treatment with glucoamylase is carried out by diluting the liquefied starch suspension, if necessary, to a solids content of about 30 percent and then adjusting the reaction pH to a level of from about 4.0 to about 5.0 and preferably to a pH of about 4.6. A sufficient amount of a glucoamylase preparation is added to provide from about 0.12 to about 0.30 glucoamylase units per gram of dry substance starch and the suspension heated to a temperature range of from about 54° to about 62° C. for a period sufficient to obtain the desired degree of conversion. The preferred holding period is from about 30 to about 80 hours. The most preferred conditions are to hold the starch suspension at a temperature of about 58° C. for about 60 hours.

To provide a substrate suitable for isomerization, the liquor is next filtered to remove non-starch residue and the filtrate preferably evaporated to about 50 percent dry substance. A soluble salt or salts comprising glucose isomerase activators may be added to the concentrated liquor and the pH adjusted to a level of from about 7.0 to about 8.5 with a solution of sodium hydroxide. Typically, the liquor is then heated to a temperature of from about 50° to about 70° C. and held for a period of from about 20 to about 60 minutes, and refiltered to precipitate and remove suspended solids which may have formed at the higher pH level. The preferred conditions are to heat to about 60° C. and hold for about 30 minutes prior to refiltering. Prolonged heating of the saccharified liquor or heating at temperatures above about 70° C. prior to isomerization is preferably avoided, particularly following the adjustment of the pH into the alkaline range. Under alkaline conditions, such heating of the liquor prior to isomerization may produce degradation products which inhibit the activity of glucose isomerase.

Isomerization of the unrefined substrate is advantageously carried out in a continuous manner by passing the substrate under suitable conditions through a column or columns containing beds of immobilized glucose isomerase. Exemplary of suitable processes for isomerizing glucose to fructose utilizing fixed beds of immobilized glucose isomerase are those taught in U.S. Pat. Nos. 3,909,354 and 3,788,945.

In addition to the obvious economic advantages provided by elimination of the necessity for refining the hydrolysate prior to isomerization, other benefits may also be realized by practicing the present invention. Thus, by maintaining liquefaction and saccharification conditions such that low levels of non-enzymatically generated ketose sugars are produced, higher conversions of starch to glucose are obtainable. Also, as a result of maintaining a low ash content in the starting starch slurry and during subsequent processing steps, less ion exchange capacity is required to demineralize the final glucose/fructose product.

DESCRIPTION OF TERMS AND ANALYTICAL METHODS

Dextrose Equivalent

Dextrose equivalent (DE) is defined as the concentration of reducing sugars present expressed as dextrose and calculated as a percentage of the dry substance. Determined by method E-26 described in "Standard Analytical Methods of the Member Companies of the Corn Industry Research Foundation, Inc.", 1001 Connecticut Ave., N. W. Washington, D.C. 20036.

Activity of Bacterial Alpha-Amylase

The activity of bacterial alpha-amylase preparations was determined by a modification of Standard Test Method, AATCC 103-1965 "Bacterial Alpha Amylase Enzymes Used in Desizing, Assay of" published in the 1967 Edition of Technical Manual of the American Association of Textile Chemists and Colorists, Volume 43, pp B-174 and B-175.

The modifications of the published method are as follows:

(1) The buffer solution for the starch substrate was prepared by dissolving 25.3 g of c.p. sodium hydroxide and 340 g of c.p. potassium dihydrogen phosphate in water and diluting to 2-liters.

(2) 125 ml of the buffer solution was added to the cooled, pasted starch substrate before the substrate was brought to the 500 ml volume.

(3) The pH of the starch substrate was determined and, if necessary, adjusted to 6.20±0.05.

(4) A 0.025 molar calcium chloride solution was used for enzyme sample dilution. This was prepared by dissolving 11.1 g of anhydrous c.p. calcium chloride in water and bringing the volume to 4 liters.

(5) The formula for converting from BAU to liquefons is BAU×2.85=liquefons.

Glucoamylase Activity

A glucoamylase activity unit (GU) is defined as the amount of enzyme which catalyzes the production of one g of dextrose per hour at 60° C. at pH 4.5 in the procedure described below.

10 ml of a 10% solution of a partially hydrolyzed starch (such as Maltrin-10, a product of Grain Processing Co., Muscatine, Iowa), containing 20 mM acetate buffer at pH 4.5, was pipetted into a capped reactor maintained at 60° C. One ml of a glycoamylase solution, containing 0.03 to 0.15 GU was added and mixed therein, and the mixture maintained for 1 hour at 60° C. At the end of the 1 hour incubation period, enzyme action was stopped by adding a predetermined volume of 1 M sodium hydroxide so as to obtain a pH of 8.5 to 10.5. The mixture was then cooled to room temperature.

2.5 ml of the assay hydrolysate so obtained was pipetted into 25 ml of Fehling's solution prepared as described in the above cited method for DE determination. The mixture was brought to a boil and titrated with standard dextrose solution containing 5 g of dextrose per liter according to the procedure cited above for DE determination. A control mixture was prepared and titrated in the exact same manner as for the assay hydrolysate above except that the 1 ml of glycoamylase solution was added to the substrate solution after the one-hour incubation period and after the addition of sodium hydroxide solution. Glucoamylase activity was calculated as follows:

$$\frac{GU}{g} = 0.002 \, V \left( \frac{C - A}{W} \right)$$

where V is the total volume (ml) of assay hydrolysate (usually 11.2 ml); C is the ml of standard dextrose solution used in the titration of the control mixture; A is the ml of standard dextrose solution used in the titration of the assay hydrolysate; and W is the weight of enzyme per ml of the diluted enzyme solution.

Immobilized Isomerase Activity

Immobilized isomerase activity was determined by the following procedure:

An immobilized isomerase sample containing 1400–2200 IGIU was weighed out. The sample was washed into a 250 ml flask with 125 ml dextrose assay solution (previously warmed to 65° C.) and 10 ml of 0.1 M tris-hydroxymethylaminomethane (THAM) solution (pH 7.8). Dextrose assay solution contained 3.33 M dextrose, 20 mM magnesium sulfate, 10 mM sodium sulfite, 100 mM THAM, and 1 mM cobalt chloride (pH 7.8). At 65° C. this dextrose solution has a pH value of 7.0. The flask was immersed in a 65° C. water bath and shaken for 1 hour. The mixture was vacuum-filtered through a 45 mm coarse fritted glass funnel fitted with a glass fiber filter and precoated with 1 g of filter-aid. The flask and enzyme cake were rinsed with small aliquots of 100 mM THAM buffer solution (pH 7.8) totaling 100 ml.

This washed enzyme was added to a 250 ml flask containing 125 ml dextrose assay solution (previously equilibrated to 65° C.). The washed enzyme was quantitatively washed into the flask with 10 ml of 10 mM THAM buffer (pH 7.8), and the flask was shaken for exactly 60 minutes. 12.0 ml of glacial acetic acid was then added, and the acidified mixture shaken for a further 15 minutes. The mixture was vacuum-filtered through a 45 mm coarse fritted glass funnel fitted with a glass fiber filter and precoated with approximately 1 g filter-aid. The flask and the funnel contents were washed with demineralized water until approximately 400 ml of filtrate was collected. The filtrate, cooled to 25° C., was diluted to 500 ml. The rotation of the solution was determined with a 2 dm cell at 25° C. as $R_2$.

A blank was processed in the same manner as above, except no enzyme was added. The optical rotation of the blank was also determined at 25° C. as $R_1$. The degree of isomerization is calculated from the following relationship:

$$I = \frac{(R_2 - R_1)}{\alpha C_p L}$$

where $\alpha$ is the specific rotation change when fructose is completely converted to dextrose; $C_p$ is the concentration of sugar in solution (0.15 g/ml); and L is length of the polarimeter tube (2 dm).

Fixed activity units (FAU) of the isomerase activity is calculated as follows:

$$FAU/g = JC/k_f tw$$

where $k_f$ is a rate constant (1.21 l hr$^{-1}$ FAU$^{-1}$ mg glucose); t is the reaction time in hours (1 hr.); w is the weight in g of the sample; C is the initial concentration in mg per 125 ml reaction mixture (75,000 mg glucose); and J is defined as follows:

$$J = \left[ I_e \left( \frac{K_s}{C_m} + 1 \right) + I_e^2 \left( \frac{K_s}{K_p} - 1 \right) \right] \ln \left( \frac{I_e}{I_e - I} \right) - I_e I \left( \frac{K_s}{K_p} - 1 \right)$$

where
$I_e$ = degree of isomerization at equilibrium in mole fraction of fructose (0.513)
I = degree of isomerization in mole fraction of fructose
$C_m$ = initial molar concentration of glucose (3.33 M)
$K_s$ = Michaelis constant for glucose (0.7 M)
$K_p$ = Michaelis constant for fructose (1.43 M)
One IGIU is equal to 15.8 FAU's.

IGIU

IGIU is the abbreviation for International Glucose Isomerase Unit and is that amount of enzyme which will convert 1 micromole of glucose to fructose per minute in a solution initially containing 2 moles of glucose per liter, 0.02 moles of MgSO$_4$ and 0.001 mole of CoCl$_2$ per liter at a pH of 6.84 to 6.85 (0.2 M sodium maleate) and at a temperature of 60° C. Glucose isomerase determinations were carried out by the method described by N. E. Lloyd, et al., *Cereal Chem.*, 49, No. 5, pp. 544–553 (1972).

Determination of Saccharides

Analysis of the hydrolysates for glucose, fructose, maltulose, and other saccharides was carried out using high pressure liquid chromatography. The procedure is described in *Standard Analytical Methods*, Corn Refiner's Association, Inc., Method E-61.

Degree of Isomerization (% Fructose)

The percent fructose obtained as a result of the isomerization reactions was determined as follows: A 5 ml aliquot of the substrate (the unrefined hydrolysate, before isomerization) was pipetted into a 100 ml volumetric flask and diluted to volume with deionized water to give a concentration of about 2.5 g dry substance per 100 ml. A 5 ml aliquot of the effluent from a column containing immobilized glucose isomerase through which the substrate has been passed was also diluted to 100 ml with deionized water. The optical rotation was determined for the diluted substrate(s) and effluent (i).

A constant (K) was derived whereby:

$$K = \frac{d \times 100}{L([\alpha_d] - [\alpha_f])}$$

K=59.08
where:
d=dilution=20
L=polarimeter cell length=0.2000 dm
$[\alpha_d]-[\alpha_f]$=change in specific rotation for converting pure glucose to pure fructose measured with a mercury light source=169.3 degrees.
Therefore:
% fructose,d.b.=59.08 $(\alpha_s - \alpha_i)/C$
where:
$\alpha_s$=observed rotation of substrate in degrees
$\alpha_i$=observed rotation of effluent in degrees
C=grams of dry substance per ml of substrate

Determination of the Stability of Glucose Isomerase

Calculation of Reaction Rate ($k_f$) and Enzyme Half-Life ($\tau$)

The stability or half-life of glucose isomerase was determined for the isomerization reactions described herein by substitution of the appropriate values into the following equation:

$$\ln\left(\frac{I_e - I_o}{I_e - I}\right) = \frac{k_f E_t e^{-0.693t/\tau}}{CR}$$

where:
$I_o$=degree of isomerization of reactor feed, F/(F+G)[1]
I=degree of isomerization of reactor effluent, F/(F/G)
$I_e$=I at equilibrium, 0.514 @ 65° C. or 0.505 at 60° C.
$k_f$=initial reaction rate constant, g(G+F)hr$^{-1}$IGIU$^{-1}$
$E_t$=enzyme activity, IGIU
C=substrate concentration, glucose, g/ml R=flow rate, ml/hr
$\tau$=half-life of enzyme, hours
t=reactor service time, hours

[1] F=weight fraction of fructose, based on total carbohyrate dry substance. G=weight fraction of glucose, based on total carbohydrate dry substance.

$k_f$, the initial reaction rate constant, and tau ($\tau$) were calculated by rearranging the above equation as follows:

$$\log\left[R \ln\left(\frac{I_e - I_o}{I_e - I}\right)\right] = \log\frac{k_f E_t}{C} - 0.30102 t/\tau$$

The slope of a plot of log:

$$\left[R \ln\left(\frac{I_e - I_o}{I_e - I}\right)\right]$$

versus time is equal to $-0.30102/\tau$; hence, $\tau = -0.30102/\text{slope}$. The intercept ($X_o$) at time 0, of such a plot is used to solve $$X_o = R \ln\left(\frac{I_e - I_o}{I_e - I}\right)$$

for the initial reaction rate $k_f$. Thus, $$k_f = \frac{C \times 10^{X_o}}{E_t},$$

The product of the initial reaction rate constant ($k_f$) and the factor expressing the half-life of the enzyme ($\tau$) provides a suitable indication of the overall efficiency of the process; the higher the value obtained for $k_f\tau$, the greater the efficiency of the process in terms of the rate of conversion of glucose to fructose and of the effect of the process on enzyme half-life.

The following examples are illustrative of the invention and are not intended to limit the scope of the invention or the ambit of the claims.

EXAMPLE 1

This example illustrates the process of the present invention carried out in a continuous manner and demonstrates the high stability of the glucose isomerase achieved by the process. The glucose isomerase utilized in this and the succeeding examples was immobilized on DEAE cellulose as described in U.S. Pat. No. 3,788,945.

Corn starch recovered from a corn wet milling operation was washed with deionized water and a slurry thereof prepared containing 33 percent dry substance starch. The pH of the slurry was adjusted to 5.2 with MgO and a sufficient amount of alpha-amylase (Termamyl-60L) added to provide 7 liquefons of alpha-amylase activity per gram of dry substance starch. The slurry was passed to a ½ inch diameter stainless steel coil and maintained therein at a temperature of 86° C. for a period of 2.5 hours. Following this first stage heat treatment, the slurry was pumped into a ½ inch diameter stainless steel coil and maintained therein at a temperature in the range of about 115° to 130° C. and at a pressure of from 50 to 100 psi for a period of about 1 minute. The slurry was then cooled to a temperature of about 86° C., dosed with the same amount of the alpha-amylase as was added in the first heating stage, and passed to a third heating coil. In this coil, which had the same characteristics as the first stage heating coil, the slurry was heated at a temperature of 86° C. for a period of 2 hours.

The liquefied starch was diluted to 30 percent dry solids content with deionized water and subjected to saccharification conditions in a multi-stage stirred tank reactor system. Sufficient filter aid (Dicalite CP-175, GREFCO, INC.) was added to provide a one percent concentration thereof, dry basis, and the pH adjusted to about 4.5 with HCl. The liquefied starch preparation was charged into the first reactor in the system and a sufficient amount of a glucoamylase preparation (AMG-150, Batch SN 3075, Novo Enzyme Corp.) added to provide 0.27 glucoamylase unit (GU) per gram of dry substance starch. The reactor contents were heated at a temperature of 58° C. and then passed serially to each of seven additional reactors maintained at the same temperature. Average residence time in each reactor was 7.5 hours. At the conclusion of the saccharification cycle, the reactor product or liquor was passed through a filter precoated with filter aid at a reduced pressure of 10 inches of mercury in order to remove any non-starch residue present.

To provide a substrate suitable for isomerization with glucose isomerase, the liquor was concentrated to about 50 percent dry substance in a continuous evaporator. The liquor was first heated to 86° C. and held at this temperature for four minutes following which evaporation was effected at 58° C. under an applied vacuum of 25 inches of mercury. A solution of $Mg(HSO_3)_2$ was added in sufficient amount to provide a 0.002 molar concentration thereof in the liquor which was then adjusted to a pH of 7.8 (determined at 25° C.) with a solution of NaOH. The substrate liquor was next pumped through a mixing coil and through a filter fitted with Whatman No. 3 filter paper, the coil and the filter being maintained at a temperature of 58° C.

Isomerization was carried out by pumping the filtered substrate directly through four fixed bed reactors connected in series and maintained at a temperature of 60° C. The reactors comprised glass columns, one inch in diameter and six inches long, charged with varying amounts of immobilized glucose isomerase. The amount of glucose isomerase activity loaded into each reactor ranged from 2,300 to 5,000 IGIU. The reactors were operated under conditions whereby a system was simulated in which spent reactors are removed from the lead position and fresh reactors are added in the trailing position. Isomerization was carried out at an input flow rate of 2.4 ml of substrate per minute to provide a fructose concentration in the final effluent of from 42 to 46 percent. At the conclusion of the residence time in each reactor, the effluent was sampled to provide relevant data. The results of the isomerization of the unrefined hydrolysate are shown in Table I.

TABLE I

| Continuous Process For Enzymatic Isomerization of Unrefined Hydrolysates; Effect on Enzyme Stability | | | | |
|---|---|---|---|---|
| Reactor (in series) | $E_o$ (IGIU) | Isomerization Period (hours) | Rate Constant $k_f^{(1)}$ | Enzyme Half-Life $\tau$(hours) | Enzyme Efficiency $k_f\tau^{(2)}$ |
| 1 | 2300 | 720 | 0.160 | 810 | 13.0 |
| 2 | 3075 | 1320 | 0.150 | 1000 | 15.0 |
| 3 | 4150 | 1320 | 0.160 | 1140 | 18.2 |
| 4 | 5000 | 1320 | 0.160 | 1060 | 17.0 |

TABLE I-continued

| Continuous Process For Enzymatic Isomerization of Unrefined Hydrolysates; Effect on Enzyme Stability | | | | |
|---|---|---|---|---|
| Reactor (in series) | $E_o$ (IGIU) | Isomerization Period (hours) | Rate Constant $k_f^{(1)}$ | Enzyme Half-Life $\tau$(hours) | Enzyme Efficiency $k_f\tau^{(2)}$ |
| 5[3] | 6000 | 600 | 0.159 | 1030 | 16.4 |
| | | weighted average: | 0.158 | 1030 | 16.3 |

[1] $g(G + F)IGIU^{-1}hr^{-1}$
[2] $g(G + F)IGIU^{-1}$
[3] Reactor No. 1 was removed from the lead position after 720 hours of operation and Reactor No. 5 was then placed in the trailing position.

Periodic analysis of the isomerized liquor provided the following average values based on the weight of dry substance:

| | |
|---|---|
| Fructose, % | 44.3 |
| Glucose, % | 51.6 |
| $DP_{2+}$, % | 4.1* |
| Calcium, ppm | 30 |
| Sulfated ash, % | 0.28 |
| Dry substance, % | 48.6 |

*includes di- and higher saccharides

The above data and those in Table I indicate that a glucose/fructose syrup containing a high proportion of fructose may be prepared by subjecting an unrefined starch hydrolysate, obtained under the specified conditions, to isomerization with immobilized glucose isomerase. The data also indicate that under the said conditions, the enzyme exhibits good stability or half-life ($\tau$) and a high degree of enzyme efficiency ($k_f\tau$) is attained.

EXAMPLE II

This example illustrates the effects of varying conditions for liquefying and saccharifying starch on the formation of non-enzymatically generated ketose sugars in the glucose-containing substrate and on the stability of glucose isomerase used to isomerize the glucose to fructose.

Starch was liquefied in separate experiments utilizing in one an alpha-amylase preparation derived from *B.licheniformis* and in the other a more highly calcium dependent alpha-amylase preparation derived from *B.subtilis*. Liquefaction was carried out in two stages of enzyme treatment with an intervening autoclave treatment to provide partial hydrolysates which were substantially free of granular or ungelatinized starch.

Two identical starch slurries each containing 33 percent dry substance were prepared. One slurry, Substrate A, was treated with *B.licheniformis* derived alpha-amylase under the liquefaction conditions which characterize the present invention. The other slurry, Substrate B, was treated with a *B.subtilis* derived alpha-amylase preparation (Dex-Lo-HC, Wallerstein Co.) and was subjected to the preferred conditions commonly employed to liquefy starch when this enzyme preparation is used.

Conditions under which the separate liquefactions were carried out are shown in Table II.

TABLE II

| | Alpha-amylase source | |
|---|---|---|
| Liquefaction Conditions | SUBSTRATE A (*B. licheniformis*) | SUBSTRATE B (*B. subtilis*) |
| pH | 5.2 | 6.6 |

TABLE II-continued

| Liquefaction Conditions | Alpha-amylase source | |
|---|---|---|
| | SUBSTRATE A (B. licheniformis) | SUBSTRATE B (B. subtilis) |
| pH adjusted with- | MgO | CaO |
| First stage | | |
| liquefons g$^{-1}$ dss | 14 | 33 |
| temperature, °C. | 86 | 88 |
| time, hours | 1 | 1 |
| Autoclaving | | |
| temperature, °C. | 125 | 150 |
| time, min. | 1 | 1 |
| Second stage | | |
| liquefons g$^{-1}$ dss | 10 | 11 |
| temperature, °C. | 86 | 88 |
| time, hours | 1 | 1 |

The liquefied starch preparations were each diluted to 30 percent dry substance, adjusted to pH 4.3, and dosed with 0.41 L GU g$^{-1}$ dss of glucoamylase. Saccharification was carried out at 58° C. for periods of 32 hours (for Substrate A) and 55 hours (for Substrate B). The saccharified liquors were filtered and evaporated to 50 percent dry substance under vacuum at a temperature of 35° C.

Three substrates were prepared for isomerization with immobilized glucose isomerase. Substrate (A) was made 0.0025 M in Mg(HSO$_3$)$_2$ and the pH was adjusted to 7.8 with NaOH solution. Substrate (B) was first treated with a stoichiometric amount of oxalic acid at pH 4.8. The calcium content of the substrate was reduced to 30 ppm based on dry substance. The liquor was then refiltered and the filtrate made 0.0025 M in Mg(HSO$_3$)$_2$. Finally, the pH of this substrate was adjusted to 6.0 with MgO and then to 7.8 with NaOH. Substrate (C) was prepared by dissolving a sufficient amount of crystallized dextrose in deionized water to provide a solution containing 50 percent dry substance dextrose. The solution was made 0.0025 M in Mg(HSO$_3$)$_2$ and adjusted to pH 6.0 with MgO and then to pH 7.8 with NaOH.

The substrates were subjected to isomerization conditions by being passed through jacketed glass columns (1 inch × 12 inches) maintained at a temperature of 65° C. each containing about 800 IGIU immobilized glucose isomerase. The substrates were introduced into the columns in a descending direction at a flow rate of 0.3 ml per minute. The isomerizations were carried out continuously for 17 days. The substrates and column effluents were sampled daily to determine the concentrations of fructose and glucose in the substrates, and the kinetic parameters of the isomerization reactions were calculated. Neither substrate (A) nor substrate (B) was subjected to a refining procedure prior to isomerization. The results are shown in Table III.

TABLE III

Effects of Conditions for Liquefaction and Saccharification on the Composition of Saccharified Substrates and on the Stability of Glucose Isomerase

| | Substrate (A) | Substrate (B) | Substrate (C) |
|---|---|---|---|
| Glucose, % d.b. | 96.6 | 96.6 | 99.8 |
| Maltulose, % d.b. | <0.1 | 0.3 | <0.1 |
| Ketose Mole Ratio | <0.05 | 0.15 | <0.05 |
| Rate Constant - k$_f$[1] | 0.025 | 0.022 | 0.025 |
| Enzyme Half-Life - τ(hours) | 700 | 470 | 585 |
| Enzyme Efficiency - k$_f$τ[2] | 17.4 | 10.1 | 14.7 |

[1] g(G + F)IGIU$^{-1}$hr$^{-1}$
[2] g(G + F)IGIU$^{-1}$

The data in Table III show that the best enzyme stability and conversion efficiency were obtained when the unrefined isomerization substrate contained a low level of maltulose. Substantially lower values for stability and efficiency were obtained using unrefined substrate (B) which contained a higher level of maltulose and was prepared under conditions of high pH and high autoclave temperature, conditions normally associated with the use of B.subtilis alpha-amylase. Results of the isomerization reaction utilizing crystallized dextrose as substrate indicate that this material was not entirely free of constituents which inhibit the activity of glucose isomerase and, thus, lend further emphasis to the importance of the conditions under which the unrefined substrate is prepared.

EXAMPLE III

This example illustrates the effects of pH and autoclaving temperature employed during starch liquefaction on the stability of the isomerizing enzyme and on the efficiency of the conversion reaction.

Five identical cornstarch samples (33 percent dry substance) were liquefied using Termamyl-60L alpha-amylase in a two stage procedure under varying conditions of pH and autoclaving temperature which are enumerated in Table V.

The samples were liquefied under the following conditions of time, temperature, and enzyme dosage shown in Table IV:

TABLE IV

| | First Stage | Second Stage |
|---|---|---|
| Enzyme dosage, (liquefons alpha-amylase g$^{-1}$ dss) | 8 | 6 |
| Temperature, °C. | 86 | 86 |
| Time, hours | 2.5 | 2.0 |
| Autoclaving time between stages = 1 minute. | | |

Twenty liters of each of the liquefied starch samples were saccharified using a glucoamylase preparation (AMG-150 Batch SN 3068, Novo Enzyme Corp.) at a dosage rate of 0.41 GU g$^{-1}$ dss. The samples were adjusted to pH 4.3 and heated at 58° C. for a period of 32 hours. The saccharified liquors were filtered and evaporated to 50 percent dry substance and adjusted to pH 6.5 with MgO. Each sample was then made 0.0025 M in Mg(HSO$_3$)$_2$ and finally adjusted to pH 7.8 (determined at 25° C.) with NaOH. The liquors were analyzed for glucose and maltulose, and the mole ratio of ketose sugars determined.

The unrefined liquors were isomerized by passage through one-inch diameter glass columns maintained at 60° C. and containing immobilized glucose isomerase at a flow rate of 0.3 ml min.$^{-1}$. Total activity of the enzyme in each column was 800 IGIU. Results of the isomerizations are given in Table V.

It is apparent that the maltulose content of the substrates was affected by both the liquefaction pH and the autoclaving temperature. As shown by the data in Table V, maltulose content varied in an inverse manner in relation to isomerase half-life, indicating that liquefaction conditions which promote the non-enzymatic formation of maltulose precursors also adversely affect enzyme stability. The data also indicate that the amount of glucose formed during saccharification is unfavorably related to the maltulose concentration.

TABLE V

Effects of Liquefaction pH and Autoclave Temperature on Stability of Glucose Isomerase and on Conversion Efficiency

| Sample No. | Liquefaction Variables | | Isomerization Substrate | | | | |
|---|---|---|---|---|---|---|---|
| | pH | Autoclave temp. (°C.) | Maltulose % d.b. | Glucose % d.b. | Ketose Mole Ratio[1] | Enzyme Half-Life $\tau$(hours) | Enzyme Efficiency $k_f\tau^{(2)}$ |
| 1 | 5.2 | 125 | <0.05 | 95.8 | <0.025 | 577 | 13.2 |
| 2 | 5.2 | 160 | 0.18 | 95.3 | 0.09 | 456 | 10.1 |
| 3 | 7.2 | 125 | 1.10 | 94.9 | 0.55 | 412 | 11.2 |
| 4 | 7.2 | 160 | 2.83 | 92.7 | 1.42 | 290 | 7.1 |
| 5 | 8.0 | 170 | 3.90 | 92.0 | 1.95 | 243 | 6.6 |

[1]Moles ketose per 100 moles anhydrohexose
[2]g(G + F)IGIU$^{-1}$

EXAMPLE IV

This example illustrates the effect of the temperature at which the unrefined substrate is heated prior to isomerization on the stability of glucose isomerase and the efficiency of the isomerization reaction.

Starch was liquefied under the conditions shown in Example I and saccharified under the conditions set forth in Example III. The saccharified liquor was filtered using Dicalite filter aid and the filtrate evaporated to 50 percent dry substance. To the concentrated liquor was added a sufficient amount of a 5 percent solution of Mg(HSO$_3$)$_2$ to make the substrate 0.0025 M therein and the pH adjusted to 7.8 at 25° C. with NaOH.

Portions of the substrate were pumped through a one-inch jacketed column maintained at one of the temperatures shown in Table VI. After a residence period of 30 minutes in a column maintained at one of the specified temperatures, the substrates were cooled, filtered, and analyzed for glucose and ketose sugars. A portion of the alkaline substrate which was not heated was similarly analyzed.

The substrate portions were isomerized individually, without prior refining thereof, by passage through jacketed glass columns maintained at 65° C., each containing a bed of immobilized glucose isomerase having an activity of 800 IGIU's. The isomerizations were carried out for a period of 500 hours at a substrate flow rate into the columns of 0.3 ml per minute. The results are shown in Table VI.

The data in Table VI indicate that higher treatment temperatures promote the formation of non-enzymatically generated ketose sugars, particularly fructose, in substrates prepared under the preferred conditions of liquefaction and saccharifaction. Concomitantly, the concentration of glucose in the substrate is reduced.

TABLE VI

Effect of Substrate Heat Treatment on Stability of Glucose Isomerase and on Conversion Efficiency

| Temp. (°C.) | Substrate Analysis | | | | Enzyme Half-Life $\tau$(hours) | Enzyme Efficiency $k_f\tau^{(2)}$ |
|---|---|---|---|---|---|---|
| | Glucose % d.b. | Maltulose % d.b. | Non-Enzyme Fructose % d.b. | Mole Ratio[1] | | |
| Ambient | 95.3 | <0.05 | 0.10 | 0.10 | — | — |
| 70 | 94.8 | <0.05 | 0.43 | 0.43 | 484 | 11.4 |
| 80 | 93.8 | <0.05 | 1.35 | 1.35 | 351 | 8.5 |
| 90 | 91.9 | 0.07 | 3.38 | 3.42 | 220 | 4.6 |
| 100 | 89.5 | 0.10 | 5.84 | 5.89 | 85 | 2.0 |

[1]Moles ketose per 100 moles anhydrohexose
[2]g(G + F)IGIU$^{-1}$

EXAMPLE V

This example illustrates the effects on the stability of glucose isomerase and on conversion efficiency of isomerizing an unrefined starch hydrolysate prepared by a recognized prior art process.

A process for preparing starch hydrolysates is taught in the hereinabove noted article by Aschengreen (Process Biochemistry, May 1975) wherein it is emphasized that thorough refining of the substrate is required to remove therefrom materials which inhibit the activity of glucose isomerase.

Starch obtained from a corn wet milling operation was slurried in deionized water to 33 percent dry substance. The slurry pH was adjusted to 6.5 with MgO and a sufficient amount of an alpha-amylase preparation derived from B.licheniformis (Termamyl-60L) added to provide therein 20 liquefons g$^{-1}$ dss. Liquefaction was affected by pumping the slurry at a rate of 12 ml per minute through coils of stainless steel tubing wherein the slurry was maintained at a temperature of from 105° to 107° C. for a period of seven minutes. The slurry was then cooled to 95° C. and held at that temperature for 1.5 hours in a second coil. The partial hydrolysate (33 percent dry substance), which had a DE of 18.6 and was free of raw starch by iodine test, was held at 60° C. prior to saccharification.

The liquefied starch was diluted to 30 percent dry substance, the pH adjusted to 4.5 and a sufficient amount of a glucoamylase preparation (Novo AMG-150) added to provide 0.25 GU per gram dss. The digest was heated for 48 hours at a temperature of 60° C. while being maintained at the above pH. The saccharified liquor was then filtered using Dicalite CP-175 filter aid and the filtrate was concentrated to 49.6 percent dry substance in a vacuum evaporator at a temperature of 43° C. Analysis of the liquor indicated a glucose content of about 95 percent and a maltulose content of about 0.2 percent.

To prepare a substrate for isomerization, the liquor was made 0.002 M in Mg(HSO$_3$)$_2$ and the pH adjusted to 7.9 with a solution of NaOH. The liquor was maintained at 65° C. for 20 minutes and then filtered.

The substrate was subjected to isomerization was immobilized glucose isomerase without prior refining or purification treatments. Isomerization was carried out by passing the substrate at an input flow rate of about 0.4 ml per minute through a one inch diameter column maintained at 65° C. and containing a bed of immobilized glucose isomerase having an activity of 1000 IGIU. Isomerization was carried out for a period of 570 hours. A solution of crystallized dextrose was isomerized under the same conditions as a control. The results are shown in Table VII.

These results demonstrate that a substrate low in calcium and non-enzymatically generated ketose sugars does not require extensive refining prior to isomerization. This is in direct contrast to accepted teachings in the art.

TABLE VII

Effects on Glucose Isomerase Stability and Conversion Efficiency of Isomerizing a Prior Art Starch Hydrolysate without Prior Refining

| Substrate | Substrate Analysis | | | Rate Constant $k_f^{(2)}$ | Enzyme Half-Life $\tau$(hours) | Enzyme Efficiency $k_f\tau^{(3)}$ |
|---|---|---|---|---|---|---|
| | Glucose % d.b. | Maltulose % d.b. | Ketose Mole Ratio$^{(1)}$ | | | |
| Control | 99.8 | <0.10 | <0.05 | 0.026 | 528 | 13.7 |
| Prior Art Substrate | 94.9 | 0.19 | 0.10 | 0.021 | 545 | 11.6 |

$^{(1)}$Moles ketose per 100 moles anhydrohexose
$^{(2)}$g(G + F)hr$^{-1}$IGIU$^{-1}$
$^{(3)}$g(G + F)IGIU$^{-1}$

EXAMPLE VI

This example illustrates the isomerization of an unrefined starch hydrolysate prepared by an acid-enzyme conversion process.

Starch obtained from a corn wet milling operation was slurried in deionized water to 33 percent dry substance. The slurry was adjusted to pH 2.2 with concentrated hydrochloric acid. Liquefaction was effected by pumping the slurry under pressure through a coil of stainless steel tubing at a rate of 22 ml per minute, whereby the slurry was maintained at a temperature of from 135° to 140° C. for a period of about four minutes and subsequently released to atmospheric pressure. The pH was adjusted to a range of 4.0–4.4 by the continuous addition of sodium hydroxide solution and the temperature reduced at 60° C. The average D.E. of the liquefied starch was 18.

About 70 liters of the liquefied starch was saccharified, filtered, and concentrated as described in Example V, except that the pH was 4.4 and total saccharification time was about 62 hours. The saccharified liquor, at 50.3% d.s., was adjusted to pH 5.8 with MgO, after which sufficient Mg(HSO$_3$)$_2$ was added to produce a 0.002 molar concentration, and the pH further adjusted to 7.8 with sodium hydroxide. The saccharified liquor was then heat treated, filtered, and isomerized under the conditions described in Example V. The isomerization was carried out for a period of 667 hours.

The results shown in Table VIII compare an isomerized crystallized dextrose substrate with the unrefined acid-enzyme substrate.

TABLE VIII

Isomerization of an Unrefined Acid-Enzyme Starch Hydrolysate

| Substrate | Substrate Analysis | | | Constant $k_f^{(2)}$ | Enzyme Half-Life (hours) | Enzyme Efficiency $k_f^{(3)}$ |
|---|---|---|---|---|---|---|
| | Glucose % d.b. | Maltulose % d.b. | Ketose Mole Ratio$^{(1)}$ | | | |
| Crystallized dextrose (Control) | 99.8 | <0.10 | <0.05 | 0.026 | 528 | 13.7 |
| Acid-Enzyme | 90.6 | <0.10 | <0.05 | 0.023 | 551 | 12.7 |

$^{(1)}$Moles ketose per 100 moles anhydrohexose
$^{(2)}$g(G + F)hr$^{-1}$IGIU$^{-1}$
$^{(3)}$g(G + F)IGIU$^{-1}$ These results demonstrate that a starch hydrolysate produced by an acid-enzyme process which is low in non-enzymatically generated ketose sugars can be efficiently isomerized without prior refining.

EXAMPLE VII

This example illustrates the use of glucose isomerase derived from a *Bacillus coagulans* microorganism to isomerize glucose to fructose in the process of the invention.

Two starch hydrolysates were prepared under the same conditions as described in Example III, except for the liquefaction pH and autoclave temperature. These conditions used for each preparation, A and B, are shown in Table IX.

TABLE IX

| | Preparation A | Preparation B |
|---|---|---|
| Liquefaction pH | 5.2 | 6.7 |
| Autoclave Temp (°C.) | 125 | 150-160 |

Analysis of the starch hydrolysates for maltulose content showed a content of <0.1 percent for preparation A and an average of 1.10 percent for preparation B.

Each preparation was filtered and concentrated to 50 percent dry substance under vacuum and was then made 0.0025 M in Mg(HSO$_3$)$_2$ after which the pH was adjusted to 7.9 with sodium hydroxide solution. The unrefined starch hydrolysate preparations were each continuously passed through a coil heated at 60° C., at a rate of 0.4 ml per minute, giving a residence time of 20 minutes, filtered and then subjected to isomerization by being passed through a jacketed glass column maintained at 65° C. at a flow rate of 0.4 ml per minute. Each column contained a bed of immobilized glucose isomerase (Sweetzyme-Type S, Batch No. 70122, manufactured by Novo Industrie, Denmark) having a total activity of 800 IGIU.

The results are shown in Table X.

TABLE X

| Prep. | Operation (hours) | Maltulose % d.b. | Ketose Mole Ratio$^{(1)}$ | Rate Constant $k_f^{(2)}$ | Enzyme Half-Life $\tau$(hours) | Enzyme Efficiency $k_f\tau^{(3)}$ |
|---|---|---|---|---|---|---|
| A | 871 | <0.1 | <0.05 | 0.0260 | 947 | 24.2 |
| B | 660 | 1.10 | 0.55 | 0.0262 | 551 | 14.4 |

$^{(1)}$Moles ketose per 100 moles anhydrohexose
$^{(2)}$g(G + F)hr$^{-1}$IGIU$^{-1}$
$^{(3)}$g(G + F)IGIU$^{-1}$ The data in Table X demonstrate the importance of maintaining conditions which result in a low concentration of maltulose in the unrefined hydrolysate.

The positive effects on the stability of glucose isomerase and on overall conversion efficiency accruing from the use in isomerization reactions of starch hydrolysates prepared by the process of the present invention make it possible to eliminate the need for refining the hydrolysates prior to isomerization. By carefully controlling conditions under which starch is liquefied, saccharified, and handled, substrates are provided wherein the levels of materials which adversely affect the stability of the glucose isomerase are such as to make possible the economic production of glucose/fructose syrups from unrefined hydrolysates on a commercial scale.

The terms and expressions which have been employed herein are not intended to exclude any equivalents of the features shown and described or portions thereof, since it is recognized that various modifications are possible within the scope of the claimed invention.

What is claimed:

1. A process for producing a glucose/fructose syrup comprising liquefying starch at a pH of less than about 6.0 and enzymatically saccharifying the liquefied starch under controlled conditions to provide an unrefined glucose-containing hydrolysate having present not more than about 100 ppm of calcium ions based on dry substance starch and wherein the mole ratio of non-enzymatically generated ketose sugars is less than about 2 (moles per 100 moles of hexose units), treating the hydrolysate to remove non-starch material therefrom, and contacting the unrefined hydrolysate with immobilized glucose isomerase to convert at least a portion of the glucose to fructose.

2. A process according to claim 1, wherein the glucose-containing hydrolysate is prepared by the acid-enzyme process.

3. A process according to claim 1, wherein the glucose-containing hydrolysate is prepared by the enzyme-enzyme process.

4. A process according to claim 3, wherein the starch is liquefied using an alpha-amylase preparation having a reduced dependence on the presence of calcium ions.

5. A process according to claim 4, wherein the alpha-amylase preparation is derived from *Bacillus licheniformis*.

6. A process according to claim 1, wherein the starch is liquefied in the presence of a calcium ion concentration of not more than about 30 ppm.

7. A process according to claim 3, wherein the starch is liquefied in two stages and there is an intervening autoclaving stage.

8. A process according to claim 7, wherein each of the two liquefaction stages is carried out at a temperature in the range of from about 82° to about 95° C. for a period in the range of from about 1 to about 3 hours.

9. A process according to claim 8, wherein each of the two liquefaction stages is carried out at a temperature in the range of from about 84° to about 88° C. for a period in the range of from about 1 to about 3 hours.

10. A process according to claim 9, wherein the first liquefaction stage is carried out at a temperature of about 86° C. for a period of about 2.5 hours and the second liquefaction stage is carried out at a temperature of 86° C. for a period of about 2 hours.

11. A process according to claim 7, wherein the starch is liquefied at a pH in the range of from about 5.0 to about 6.0.

12. A process according to claim 11, wherein the starch is liquefied at a pH in the range of from about 5.2 to about 5.4.

13. A process according to claim 7, wherein the partially liquefied starch is autoclaved at a temperature not greater than about 160° C. for a period not greater than about 2 minutes.

14. A process according to claim 13, wherein the partially liquefied starch is autoclaved at a temperature of about 125° C. for a period of about 1 minute.

15. A process according to claim 1, wherein the starch is liquefied to a D.E. of from about 14 to about 20.

16. A process according to claim 15, wherein the starch is liquefied to a D.E. of about 16.

17. A process according to claim 1, wherein the liquefied starch is prepared by treating a starch slurry having an ionic content of not more than about 0.2 percent as sulfated ash on a dry basis.

18. A process according to claim 3, wherein the liquefied starch is saccharified under suitable conditions to provide an unrefined hydrolysate having a glucose content greater than about 92 percent based on dry substance starch.

19. A process according to claim 18, wherein the liquefied starch is saccharified to provide an unrefined hydrolysate having a glucose content greater than 94 percent based on dry substance starch.

20. A process according to claim 19, wherein the liquefied starch is treated with glucoamylase at a temperature in the range of from about 54° to about 62° C. for a period in the range of from about 30 to about 80 hours.

21. A process according to claim 20, wherein the liquefied starch is treated with glucoamylase at a temperature of about 58° C. for a period of about 60 hours.

22. A process according to claim 1, wherein the liquefied starch is treated with glucoamylase at a pH in the range of from about 4.0 to about 5.0 and preferably at a pH of about 4.6.

23. A process according to claim 1, wherein the unrefined hydrolysate is characterized as having present not more than about 30 ppm of calcium ions and a mole ratio of non-enzymatically generated ketose sugars of less than about 2.

24. A process according to claim 23, wherein the maltulose content of the unrefined hydrolysate is less than about 4 percent based on dry substance starch.

25. A process according to claim 23, wherein the non-enzymatic fructose content of the unrefined hydrolysate is less than about 2 percent based on dry substance starch.

26. A process according to claim 23, wherein the mole ratio of non-enzymatically generated ketose sugars is less than about 1.

27. A process according to claim 26, wherein the maltulose content of the unrefined hydrolysate is less than about 2 percent based on dry substance starch.

28. A process according to claim 26, wherein the non-enzymatic fructose content of the unrefined hydrolysate is less than about 1 percent based on dry substance starch.

29. A process according to claim 1, wherein prior to being contacted with immobilized glucose isomerase the unrefined hydrolysate is heated at a temperature in the range of from about 50° to about 70° C. for a period in the range of from about 20 to about 60 minutes.

30. A process according to claim 29, wherein the unrefined hydrolysate is heated at a temperature of about 60° C. for a period of about 30 minutes.

31. A process according to claim 1, wherein the unrefined hydrolysate is passed through at least one bed of immobilized glucose isomerase under suitable conditions to isomerize at least a portion of the glucose in the hydrolysate is fructose.

32. A process according to claim 31, wherein the bed of immobilized glucose isomerase comprises glucose isomerase adsorbed or bound onto DEAE cellulose.

33. A process according to claim 31, wherein the bed of immobilized glucose isomerase comprises glucose isomerase adsorbed or bound onto an anion exchange resin.

* * * * *